United States Patent
Coffin

(10) Patent No.: US 10,481,084 B2
(45) Date of Patent: Nov. 19, 2019

(54) ADVANCED REFERENCE DETECTOR FOR INFRARED SPECTROSCOPY

(71) Applicant: Thermo Electron Scientific Instruments LLC, Madison, WI (US)

(72) Inventor: John Magie Coffin, Blue Mounds, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 0 days.

(21) Appl. No.: 16/034,417

(22) Filed: Jul. 13, 2018

(65) Prior Publication Data

US 2019/0017930 A1 Jan. 17, 2019

Related U.S. Application Data

(60) Provisional application No. 62/532,513, filed on Jul. 14, 2017.

(51) Int. Cl.
  *G01N 21/3577* (2014.01)
  *G01J 3/02* (2006.01)
  (Continued)

(52) U.S. Cl.
  CPC .......... *G01N 21/3577* (2013.01); *G01J 3/021* (2013.01); *G01J 3/0208* (2013.01);
  (Continued)

(58) Field of Classification Search
  CPC .......... G01N 21/3577; G01N 21/3504; G01N 2021/3595; G01J 3/0229; G01J 3/28;
  (Continued)

(56) References Cited

U.S. PATENT DOCUMENTS

| 4,538,910 A | 9/1985 | Doyle |
| 6,031,609 A | 2/2000 | Funk et al. |

(Continued)

FOREIGN PATENT DOCUMENTS

WO 84/03558 A1 9/1984

OTHER PUBLICATIONS

Oct. 31, 2018—International Search Report and Written Opinion of PCT/US2018/041961.

*Primary Examiner* — David P Porta
*Assistant Examiner* — Meenakshi S Sahu
(74) *Attorney, Agent, or Firm* — Banner & Witcoff, Ltd.

(57) ABSTRACT

A spectroscopy system and method in which the optical path following the interferometer includes a Jacquinot stop having an aperture disposed substantially at its focal point. The Jacquinot stop includes a reflective surface substantially non-orthogonal to the longitudinal axis of the path and facing the source of the IR signal containing an interferogram. The aperture passes an inner portion of the incident IR signal, while the reflective surface reflects an outer portion. The reflected outer portion of the incident IR signal, which contains erroneous spectral information due to inherent flaws in the interferometer optics, is thereby effectively removed from the original incident IR signal ultimately used to irradiate the sample, and yet still be made available for use in monitoring background spectra of the sampling optics.

20 Claims, 3 Drawing Sheets

(51) Int. Cl.
  *G01J 3/10* (2006.01)
  *G01J 3/26* (2006.01)
  *G01J 3/45* (2006.01)
  *G01N 21/3504* (2014.01)
  *G01J 3/28* (2006.01)
  *G01N 21/35* (2014.01)

(52) U.S. Cl.
  CPC ............. *G01J 3/0229* (2013.01); *G01J 3/108* (2013.01); *G01J 3/26* (2013.01); *G01J 3/28* (2013.01); *G01J 3/45* (2013.01); *G01N 21/3504* (2013.01); *G01J 2003/2869* (2013.01); *G01N 2021/3595* (2013.01)

(58) Field of Classification Search
  CPC .. G01J 3/021; G01J 3/0208; G01J 3/45; G01J 3/26; G01J 3/108; G01J 2003/2869
  USPC .................... 250/339.01, 339.08, 339–9
  See application file for complete search history.

(56) References Cited

U.S. PATENT DOCUMENTS

| | | | |
|---|---|---|---|
| 7,755,775 B1 | 7/2010 | Li | |
| 9,557,221 B1* | 1/2017 | Manning | G01J 3/4535 |
| 2001/0035957 A1* | 11/2001 | Clermont | G01J 3/02 |
| | | | 356/451 |

* cited by examiner

ADVANCED REFERENCE DETECTOR FOR INFRARED SPECTROSCOPY

CROSS-REFERENCE TO RELATED APPLICATIONS

This application claims priority to U.S. Provisional Application Ser. No. 62/532,513, filed, Jul. 14, 2017, and entitled "ADVANCED REFERENCE DETECTOR FOR INFRARED SPECTROSCOPY", which is incorporated herein by reference in its entirety.

FIELD OF THE INVENTION

The present invention relates to detectors for use in infrared spectroscopy, and in particular embodiments, to reference detectors used in Fourier Transform infrared (FTIR) spectroscopy systems for monitoring the background spectrum.

BACKGROUND

Fourier transform infrared (FTIR) spectrometry was developed to overcome limitations of dispersive spectrometry techniques, particularly the slow scanning process. With FTIR, all infrared (IR) frequencies can be measured simultaneously, rather than individually, with a simple optical device referred to as an interferometer. An interferometer produces a unique signal containing all IR frequencies "encoded" within it. This signal can be measured very quickly, e.g., within approximately one second, thereby reducing the time element per sample to a matter of only a few seconds rather than several minutes.

Most interferometers employ a beamsplitter which receives an incoming IR beam and divides it into two optical beams. One beam is reflected by a flat mirror which is fixed in place. The other beam is reflected by a movable flat mirror which is controlled to move back and forth over a short distance (e.g., a few millimeters). The resulting two reflected beams are recombined when they meet back at the beamsplitter.

With one beam traveling a fixed path length and the other traveling a constantly changing path length (due to the mirror movement), the recombined signal exiting the interferometer is the result of these two beams "interfering" with each other. This resulting signal is referred to as an interferogram and has a unique property in that every data point (as a function of the moving mirror position) forming the signal has information about every IR frequency received from the IR source. As a result, as the interferogram is measured, all frequencies are measured simultaneously, thereby enabling extremely fast measurements.

To perform an analysis, a user requires a frequency spectrum (as a plot of received IR signal intensity at each frequency) to make an identification, which means that the measured interferogram signal cannot be interpreted directly. A form of "decoding" the individual frequencies is needed, and is done by performing a Fourier transformation with a computer which then presents the user with the desired spectral information for analysis.

In prior art FTIRs, the IR light spectra collected by the sample detector is shaped by the FTIR instrument sampling optics, and by the sample light absorption if it is placed in the sampling optics of the instrument. Since user is only interested in the light absorption caused by the sample, what is needed is a relative scale for the absorption intensity, which requires a background spectrum to be measured, normally with no sample in the beam. (This background spectrum represents characteristics of the instrument itself and the IR signal path within the instrument, e.g., water and/or carbon dioxide ($CO_2$) in the air through which the IR signal travels.) This measured background is then compared to measurements made with the sample in the beam to determine the relative transmittance (e.g., in terms of a percentage by ratioing out the shape of the stored background scan collected before the sample was placed in the sampling optics). This technique results in a measured spectrum with instrumental characteristics removed. Thus, all spectral features which are present are due to only the sample. Typically, a single background measurement is made and stored for use in multiple subsequent sample measurements.

However, performing such background spectrum measurements take extra time and is not possible if the sample cannot be removed. Hence, in cases of a fixed sample, a stored background spectrum of some age must be used. A reference detector can be used to collect some of the IR signal before it reaches the sample to enable verification that the system is scanning properly. However, since most of the light is sent to the sample, the normal reference signal is weak and can only be used for low grade verification that the system is collecting data but cannot verify that the sample data is of good quality.

Additionally, problems arise when something in the light path changes between the time the background spectrum was collected and the sample data was collected. The changes show up as errors in sample data. Exemplary changes include portions of the sample left over in the optical path due to poor cleaning. Additionally, dirt, dust, and optical mechanical damage in the sampling optics can affect the light getting to the detector on different sample runs over time, and after the testing of many samples. Temperature changes can also affect the optics by changing the light at the detector. Rapid changes in water vapor and $CO_2$ in the purge air in the light beam path can create problems as well. Purge gas can be used to reduce water vapor error in the data; however, the use of such purge gas can be expensive.

Prior art systems typically run a background spectrum measurement just before collecting sample data, and accept some water vapor error in data as an accepted standard process. It would be desirable to provide a device that reduces the need to use purge gas and the need for a separate background collection for each sample.

SUMMARY

A spectroscopy system and method in which the optical path following the interferometer includes a Jacquinot stop ("J stop") having an aperture disposed substantially at its focal point. The J stop includes a reflective surface substantially non-orthogonal to the longitudinal axis of the path and facing the source of the IR signal containing an interferogram. The aperture passes an inner portion of the incident IR signal, while the reflective surface reflects an outer portion. The reflected outer portion of the incident IR signal, which contains erroneous spectral information due to inherent flaws in the interferometer optics, is thereby effectively removed from the original incident IR signal ultimately used to irradiate the sample, and yet still be made available for use in monitoring background spectra of the sampling optics.

In accordance with an exemplary embodiment, a spectroscopy system includes: an interferogram source to provide an IR signal containing an interferogram; a source path including a focal point along a path axis of a first portion of an optical path extending from the interferogram source; a Jacquinot stop including an aperture disposed substantially at the focal point, and a reflective surface substantially non-orthogonal to the path axis and facing the interferogram source, wherein the aperture passes an inner portion of the IR signal as an incident portion of the IR signal, and the reflective surface reflects an outer portion of the IR signal as a reflected portion of the IR signal; and a reference detection device to detect the reflected portion of the IR signal.

In accordance with another exemplary embodiment, a spectroscopy method includes: generating, with an interferogram source, an IR signal containing an interferogram; conveying the IR signal via a source path including a focal point along a path axis of a first portion of an optical path extending from the interferogram source; passing an inner portion of the IR signal as an incident portion of the IR signal via an aperture of a Jacquinot stop disposed substantially at the focal point and including a reflective surface substantially non-orthogonal to the path axis and facing the interferogram source; reflecting, via the reflective surface, an outer portion of the IR signal as a reflected portion of the IR signal; and detecting the reflected portion of the IR signal.

DETAILED DESCRIPTION OF EMBODIMENTS

The following detailed description is of example embodiments of the presently claimed invention with references to the accompanying drawings. Such description is intended to be illustrative and not limiting with respect to the scope of the present invention. Such embodiments are described in sufficient detail to enable one of ordinary skill in the art to practice the subject invention, and it will be understood that other embodiments may be practiced with some variations without departing from the spirit or scope of the subject invention.

As discussed in more detail below, the presently disclosure provides a FTIR spectroscopy system with an advanced reference detector via which an IR reference signal is provided that is significantly stronger (e.g., 50-150 times) than that of conventional systems, as well as increase the IR signal in the sample compartment (e.g., 2-5%) since no light is taken from the main IR signal to feed the reference detector. This is made possible by using previously unused light that does not pass through the J stop aperture.

Figure 1:
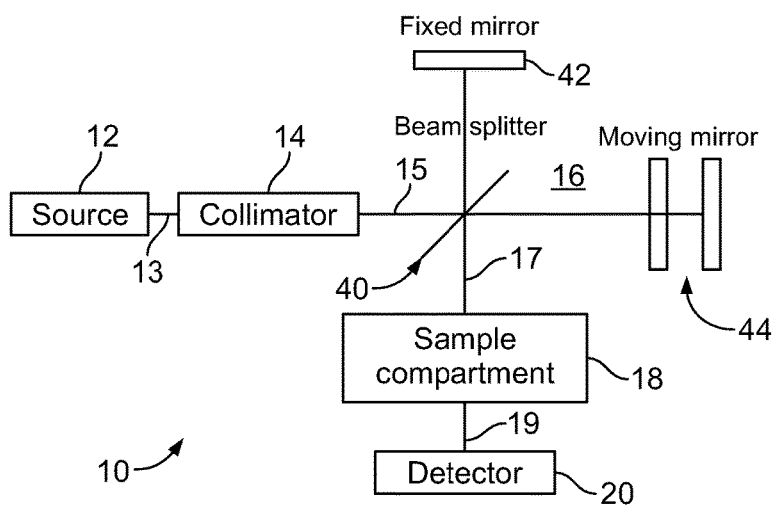
FIG. 1 depicts the elements of an FTIR spectrometer system generating an IR signal containing an interferogram for irradiating a sample.

Referring to FIG. 1, a common FTIR spectrometer includes an IR source 12, collimator 14, an interferometer 16, a sample compartment 18 and a detector 20. The interferometer 16 includes a beamsplitter 40, a fixed mirror 42 and a movable mirror 44. The source 12 generates IR radiation 13 which the collimator 14 aligns to produce parallel rays of light 15. The collimated IR signal 15 is converted to an interferogram 17 that irradiates a sample within the sample compartment 18. The resulting IR signal 19 containing energy not absorbed by the sample is detected by the detector 20 and amplified and converted to a digital signal by an amplifier and analog-to-digital converter (ADC), respectively (not shown), for processing by a computer (not shown) with which a Fourier transform is computed. (Though not shown here, also included is a laser source that provides a laser reference signal to control interferogram mirror position. As is known in the art, the zero amplitude crossings of this laser reference signal define the discrete time intervals during which the interferogram is sampled.)

Figure 2:
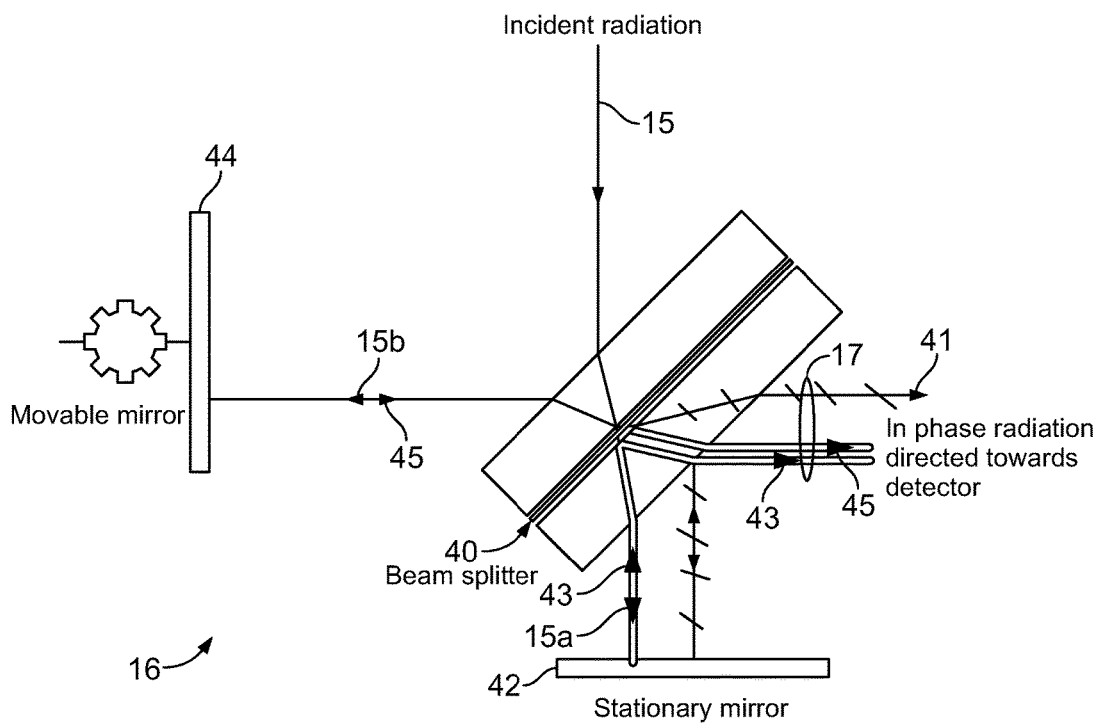
FIG. 2 depicts exemplary elements of a Michelson interferometer.

Referring to FIG. 2, the interferometer 16 is commonly implemented using a Michelson interferometer which splits the incoming beam of light into two so that the paths of the two beams are different. The Michelson interferometer recombines the two beams and conducts them on to the detector where the difference of the intensity of these two beams is measured as a function of the difference of the paths.

A typical Michelson interferometer consists of the two perpendicular mirrors, stationary 42 and movable 44, and the beamsplitter 40. The beamsplitter 40 is designed to transmit half of the light 15a and reflect half of the light 15b. Subsequently, the transmitted light 15a and the reflected light 15b strike the stationary mirror 42 and the movable mirror 44, respectively, which, in turn, reflect back previously transmitted light 43 and previously reflected light 45. When reflected back by the mirrors 42, 44, these two beams of light 43, 45 recombine with each other at the beamsplitter 40. These recombined beams of light 43, 45 form the interferogram 17, which also includes a small amount of off-axis reflected light 41 caused by imperfections in one or both of the mirrors 42, 44.

In a conventional FTIR system a Jacquinot stop ("J stop") is placed at the focal point of the interferogram 17. As is well known in the art, the J stop is a device having an aperture for passing high quality light 43, 45 (e.g., within the radially inward portion of the interferogram 17) to the sample while blocking light 41 that is sufficiently off of the center of the light beam 17 (e.g., within the radially outward portion of the interferogram 17) such that it contains erroneous information due to slightly shifted and broadened spectral lines.

These errors, which tend to be repeatable, can be measured and quantified such that, in accordance with exemplary embodiments, this relatively large amount of previously unused light can be used to provide a strong reference signal that can be used in real time to detect unwanted changes in the interferogram 17. This reference signal can be collected in real time by a second IR detector along with the light passed through the sample and processed (e.g., via computer software) to correct the sample data in real time for system and/or environmental conditions and/or changes that are typically caused by levels of and/or variations in temperature moisture, gases in the air inside the sampling area of the FTIR system, and/or aging IR source and optical components.

Figure 3:
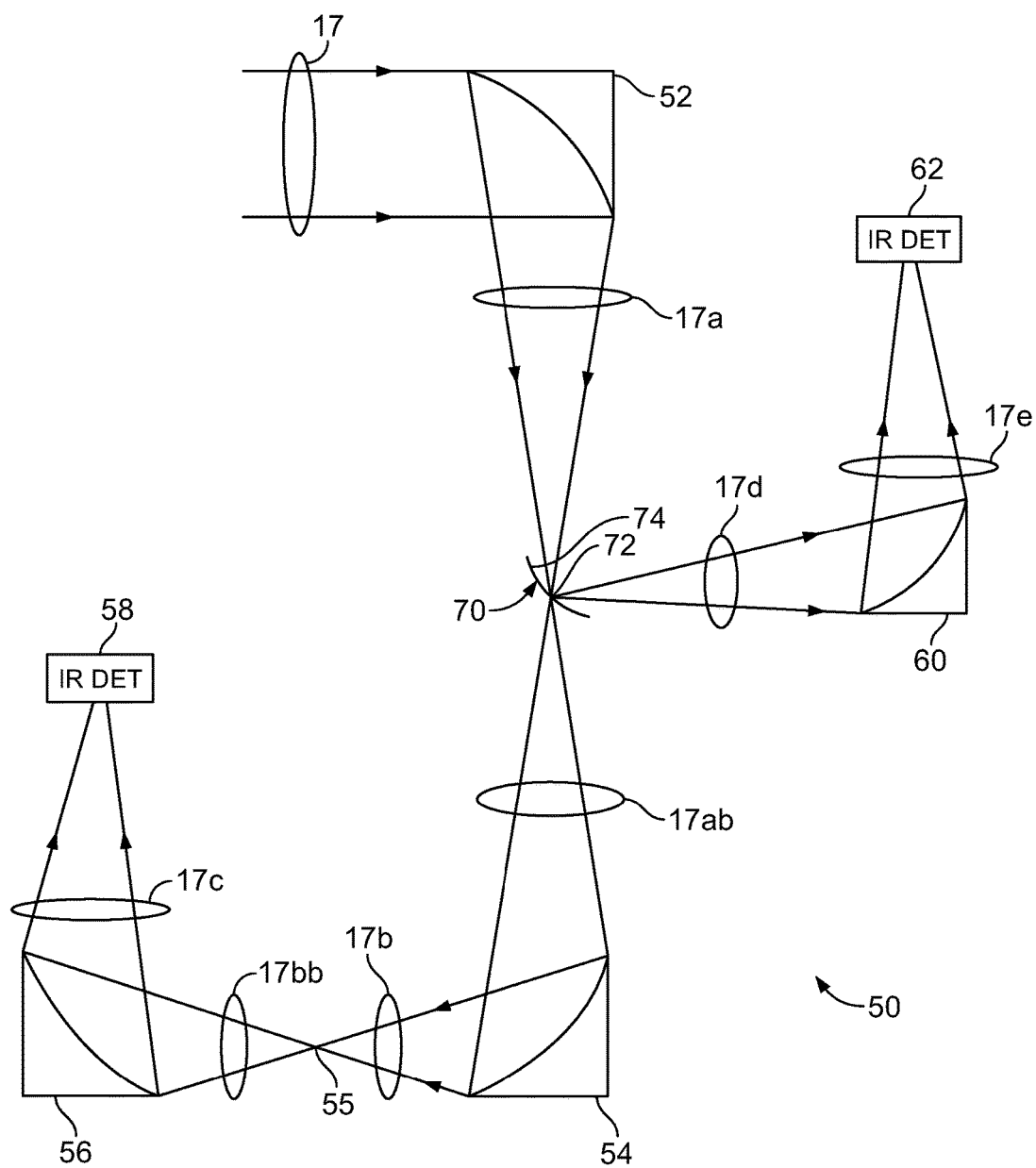
FIG. 3 depicts the output optical path for the IR signal in an FTIR spectrometer system with a reference detector in accordance with exemplary embodiments.

Referring to FIG. 3, in accordance with exemplary embodiments, a FTIR spectroscopy system includes, in addition to an IR source and interferometer as discussed above, mirrors 52, 54, 56 for defining an optical path for directing and receiving the interferogram 17 to and from, respectively, the sample region 55, and a sample detector 58 for capturing the reflected light that passes through the sample. Also included is an improved J stop 70 (discussed in more detail below) plus a reference mirror 60 and a reference detector 62. The mirrors 52, 54, 56, 60 in this exemplary embodiment are preferably elliptical mirrors to provide for point-to-point reflections.

The interferogram 17 produced by the beamsplitter 40 of the interferometer 16 (FIG. 2) is reflected by the first mirror 52 to produce the first reflected interferogram 17a. The J stop 70 is located at the focal point of the first reflected interferogram 17a. As discussed above (and below in more detail), the J stop 70 includes an aperture 72 (e.g., circular) which allows the high quality light 43, 45 (e.g., within the radially inward portion of the first reflected interferogram 17a) to continue on as a higher quality interferogram 17ab for irradiating the sample. The J stop 70 also includes a reflective surface 74 (e.g., mirrored) which is non-orthogonal to the axis of the optical path of the reflected interferogram 17a. This reflective surface 74 reflects the lower quality light 41 (e.g., within the radially outward portion of the first reflected interferogram 17a) to provide a reference beam 17d. This reference beam 17d is, in turn, reflected by the reference mirror 60 to produce a reflected reference beam 17e to be received by the reference detector 62 for enabling real time measurement of the background spectra.

The higher quality interferogram 17ab is further reflected by a second mirror 54 to produce an IR light beam 17b having a focal point 55 substantially at which the sample (not shown) is placed during testing. The resulting exit IR light beam 17bb from the sample is reflected by a third mirror 56 to produce another focus point in an IR light beam 17c to be received by the sample detector 58.

Figure 4:
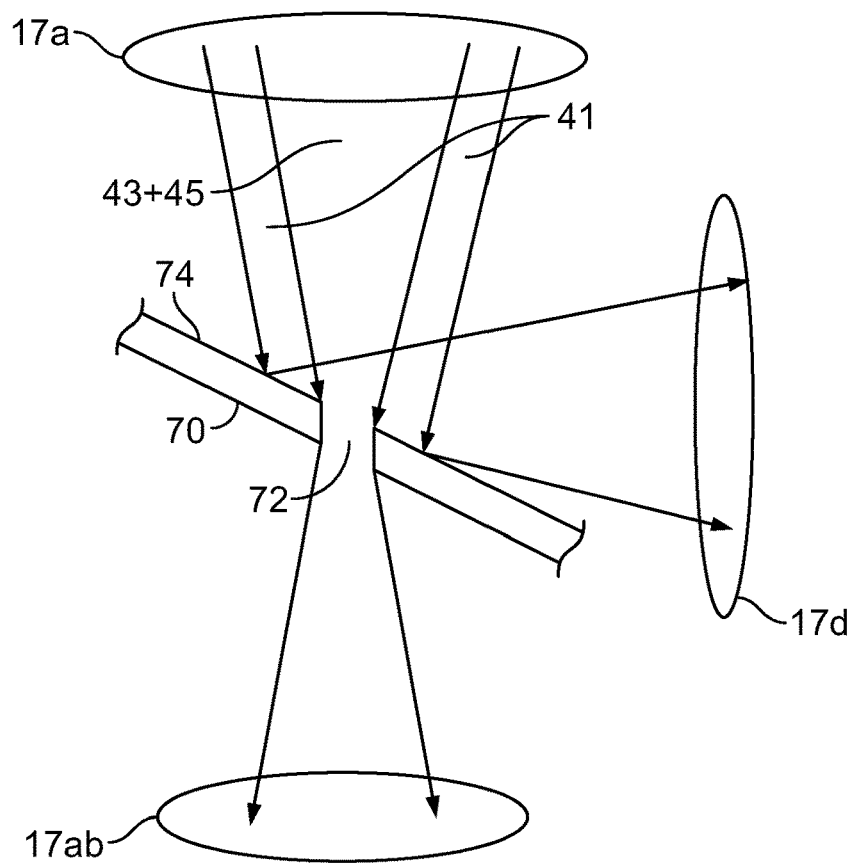
FIG. 4 depicts a more detailed view of a reference detector in accordance with exemplary embodiments.

Referring to FIG. 4, in accordance with exemplary embodiments, as discussed above, the J stop 70 is positioned in a non-orthogonal manner relative to the axis of the optical path of the reflected IR signal 17a. Its aperture 72 allows the high quality light 43, 45 to continue on as the higher quality IR signal 17ab for irradiating the sample, while its reflective surface 74 reflects the lower quality light 41 to provide the reference beam 17d.

Using an angled J stop in accordance with exemplary embodiments provides multiple advantages. For example, the resulting sample and reference IR signals provide more information to the FTIR software and firmware that allows several useful features, such as increased reliability since the bench firmware can more easily verify the location of the centerburst on each scan, and correct it and adjust interferometer alignment as needed. Automatic system validation software will have more information, thereby enabling better system validation. The host analyzer will have a significantly improved reference signal that can be used to monitor the amount of water in the system and warn the user that the desiccant or air dryer is failing before damage occurs. The host analyzer can warn the user when the sampling optics and/or windows are dirty, blocked or damaged before bad data is collected. Water and $CO_2$ suppression can be more accurate, since reference spectra is collected at the same time as the sample spectra, thereby enabling measurements of water and $CO_2$ in the system with no time error. Meaningful data collection is possible without first measuring background spectra, since the reference spectra is high quality and the reference spectra can be used (with mathematical modeling of the measured water and $CO_2$) as the background spectra, thereby reducing user collection time and workload. For example, the narrow reference spectral lines caused by the background water and $CO_2$ have small and predictable errors, as compared to the sample spectra collected by the sample detector.

Fast source turn on is enabled, since the improved reference signal allows accurate measurement of the source temperature in real time. This allows an added control system to use higher power levels controlled by the information always available from the reference detector as needed to heat up and stabilize the source in a few seconds, which allows the source to be off most of the time for most users, thereby greatly reducing heat load and allowing operation in warmer environments. Greater battery life for portable systems is enabled, since the shortened warm-up time (e.g., a few seconds) avoids a need to keep the source powered on all the time. Better system stability is realized even if the source or room temperature is not fully stabilized, since collecting background data concurrently with sample data enables better spectral corrections even in varying conditions, thereby giving a better user experience. Automatic alignment ("autotune") of the interferometer to maximize the IR signal can be enabled at all times. Reference detectors in conventional instruments only receive light from a tiny part of the beamsplitter area which results in poor quality reference detector data thereby making autotune operation very poor, and forcing the user to clear the sample compartment to obtain the needed high quality IR signal before autotune can be run. A system with a reference detector in accordance with exemplary embodiments uses the entire beamsplitter IR signal producing the needed high quality IR signal, thereby enabling autotune to run automatically even if the sample compartment is blocked.

Also, the improved source temperature control enables use of low cost, lower lifetime silicon carbide sources, since in most FTIR systems that do not collect data continuously, the source can be off most of the time, thereby greatly extending source lifetimes. The active source temperature control can automatically correct for different source resistances, which in prior art systems using fixed voltage power supplies cause varying operating temperatures, and must be compensated by using higher cost selected resistance sources. The real time information collected by the reference detector enables the use of inexpensive standard furnace igniters, which have resistances that often vary from source to source.

Similarly, a higher quality reference signal as produced by a system with a reference detector in accordance with exemplary embodiments enables use of low cost, lower sensitivity long wavelength pyroelectric detectors. This is advantageous when needing to test samples with IR signals having longer wavelengths.

Further, use of advanced total reflection (ATR) sampling becomes increasingly advantageous when combined with a reference detector in accordance with exemplary embodiments. For example, using a reference detector as discussed above in an ATR FTIR spectroscopy system enables validation of the sample path without removing the ATR crystal.

Figure 5:
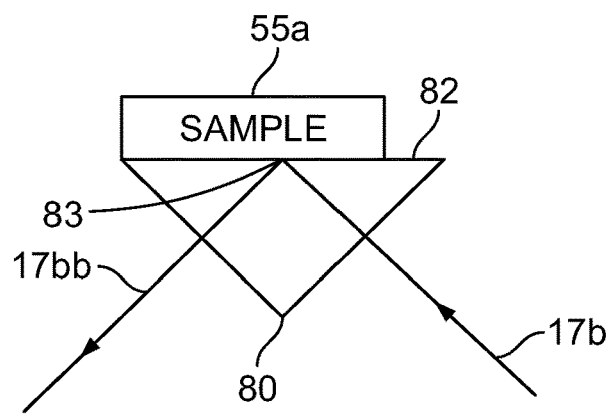
FIG. 5 depicts advance total reflection (ATR) sampling that can advantageously be used with a reference detector in accordance with exemplary embodiments to enable validation of the sample path including the ATR crystal.

Referring to FIG. 5, as is well known in the art, ATR is a sampling technique used within an IR spectroscopy system to enable samples to be examined directly in either solid or liquid state without special or further sample preparation. At the sample region 55 (FIG. 3), typically within a top surface of a sample compartment part of the system, is the ATR crystal 80 (examples of which include germanium, KRS-5, zinc selenide, silicon and, increasingly, artificial diamond due to its chemical purity and increasing affordability). Typically, the sample 55a is placed in contact with a top surface 82 of the crystal 80. The reflected IR light beam 17b (FIG. 3) enters the crystal 80 from below (e.g., at a 45 degree angle) and is reflected at the crystal-to-sample interface 83. Because of its wave-like properties, the light 17b is not reflected directly by the boundary surface 82 of the crystal 80 but by a shallow virtual layer within the surface of the sample 55a. The fraction of light reaching into the sample 55a, known as an evanescent wave, has a penetration depth (e.g., 0.5-3 microns) that is dependent upon the wavelength of the light, the refractive indices of the ATR crystal 80 and sample 55a, and angle of the entering light beam. In spectral regions where the sample 55a absorbs energy, the evanescent wave is attenuated before exiting the ATR crystal 80 (as the exiting IR light beam 17bb) and being directed to the IR detector 58. (The number of reflections may be varied by varying the angle of incidence and shape of the crystal.)

For a liquid sample, a shallow amount can be placed (e.g., poured) on the surface 82 of the crystal 80, and retained there by gravity. A solid sample is typically pressed (e.g., with some form of compressive clamp) into direct contact with the crystal. Penetration of the evanescent wave into a solid sample is improved with more intimate contact, since this clamping helps ensure that minimal trapped air is included as part of the optical path traveled by the evanescent wave, which would distort test results and/or reduce the effective signal-to-noise ratio.

As a result of this necessary physical contact between the sample 55a and crystal 80, over time, transmissivity of the crystal can become degraded, e.g., due to smearing from or residue of a liquid sample, or scratches or smudges cause by a clamped solid sample. To determine this it has been necessary to remove any remaining sample and then use the reflected IR light beam 17b (FIG. 3) as a background reference interferogram to produce a sample background IR signal to be received by the sample detector 58 to, in turn, produce detected IR data for generating a sample background spectrum in the computer (not shown). This sample background spectrum can then be compared to a previously measured and stored background spectrum (e.g., from when the crystal was first installed or when the crystal was last cleaned) for any nontrivial differences or anomalies. If any such differences or anomalies are found, it can be decided whether and/or when to clean or replace the crystal.

Hence, this requires any current testing being performed to be suspended for at least the time interval during which the new background reference spectrum is measured. Plus, this relies upon availability of a previously measured and stored background spectrum, which, in turn, generally needs to be updated or replaced, especially if and/or when any components defining the total optical path for the system (e.g., the crystal 80 or any of the mirrors 52, 54, 56) are replaced, repositioned or modified.

In contrast thereto, by also using a reference detector as discussed above, it is now possible to remove any sample and simply compare the newly generated sample background spectrum to the reference spectrum being monitored in real time. For example, this comparison can be automated by having the computer (not shown) compute deviations on a predetermined point-by-point basis between the spectra, or if a graphical user interface is available, overlaying the spectra for visual comparison by the user.

It is to be appreciated that the idea of using the reference detector signal itself as a real time background measurement is a simple and attractive alternative. However, the reference detector data does have visible artifacts that are differences caused by using light from different parts of the source. There are also slight shifts in narrow line shapes that affect gases like water vapor caused by the light going through the interferometer at a different angle than the sample light. Therefore, stored backgrounds collected through the sample optics may give better looking data.

The reference detector can reduce the user work load by allowing a stored background measurement to be used for a longer period of time by using the reference signal to validate that stored background measurement before and again at the time a sample is collected. If needed, the reference detector and the validation software can automatically autotune the system to account for temperature change and to warn the user that the sample optics are blocked, or dirty, thereby allowing the user to take corrective action before attempting to collect a sample.

Not having to run a background measurement every time a sample is collected provides a time savings and system performance improvements, thereby providing significant value and improved validation to the user.

The use of a high quality reference detector as disclosed herein allows a strong high quality reference detector signal to more reliably locate interferogram centerburst correctly using existing software and firmware.

Collecting and storing in validation software memory a known good interferogram from both a sample detector and a reference detector at the same time will provide a known good interferogram for both detectors to allow system verification in the future. Data collected in the future can be compared by validation software to make sure that the difference in the stored and new data is limited as defined in specifications. The reference detector would allow system validation software to validate the reference detector signal even if the sample is left in the sample compartment, and could at the same time allow the software to alert the user that the sample compartment has something in it.

In many FTIR systems, the validation software can read the identity of different sampling accessories. The validation software can store in memory a known good background interferogram for each different sampling accessory, and then use the stored accessory background interferogram to automatically validate the sampling accessory in a few seconds after it is inserted into the spectrometer. The validation software can check the reference detector interferogram and know that the spectrometer is valid, and then look at the sample detector interferogram and compare it to the to the stored validation standard for that accessory and be able to tell the user that the accessory and system is working satisfactorily. Alternatively, this could let the user know that the accessory interferogram is weak, which could mean that some sample remains in the accessory and accessory cleaning will fix the problem. If the accessory signal is very weak, or missing, the system software can now identify notify the user that the problem is a more serious problem with either the accessory or the sample detector.

It is to be appreciate that there may be issues with the sampling system that cannot be rectified by cleaning (e.g., window scratches). In such cases, the stored background measurement for the accessory can be updated with a new stored background measurement (with the lower throughput) by the user, who is now in a position to know that some damage has occurred. The original accessory background measurement will still be available to measure total losses even after many cleanings.

In embodiments of an FTIR system with a reference detector that use a low cost or low power source, the option of turning the source temperature down to increase both battery and source life is much improved, because the reference detector signal can be processed by the system software to accurately measure and control the source temperature. A problem with varying the source temperature in a prior art FTIR is that after start up with a cool source, the FTIR system spectra drifts for many minutes as the source heats up. With an active control, this heat up time can be reduced to between 3 and 30 seconds, depending on the particular source used. Source aging can be measured, and the software can compare the known good stored interferogram collected with a new source that is fully heated and stabilized to a recently measured interferogram and alert the user to any potential problems with the source that need to be addressed. Also, validation software can look at the reference interferogram and alert the user when the source is providing less than ideal results in order to give the user time to get the problems addressed before the system fails. This makes more possible the use of small low power sources that provide excellent battery operation but have limited lifetimes.

Because of the improved validation and automation of the FTIR instrument autotune function, the user can more confidently use a stored background measurement to save the time and work involved in collecting background measurements for each sample measurement.

For any given sampling accessory, the difference between the sample optics data and the reference optics data can be stored and automatically validated so the stored background measurement can be used for days or weeks. Validation software can be used to prompt the user to clean the sample optics if needed and to run a fresh background measurement that can be stored if this difference becomes large enough to cause the validation software to issue the prompt to collect a new background measurement.

Water vapor and $CO_2$ in the air absorb IR light and can cause artifacts, or errors, in the data that change rapidly with time. In prior art systems, even a small time difference between the collection of the background measurement and sample measurement can cause serious spectral artifacts. Most prior art FTIR instruments accept these errors, or use expensive purge gas to remove water and $CO_2$. Some prior art systems further correct these issues by using stored data and mathematical estimates of the amount of water vapor in the sample data to reduce water vapor artifacts. However, these estimates can have sizeable errors.

The use of high quality reference data as disclosed herein is much better matched in time and place, allowing the system software to have more and better data to work with in order to mathematically correct and remove the water vapor and $CO_2$ artifacts.

In certain embodiments, the reference detector signal does have systematic differences from the sample signal, which is caused by the light going through the beamsplitter at different angles that do not change over time. Therefore, this difference is very predictable, allowing mathematical correction using a stored difference between the sample and reference spectra.

The reference signal looks very similar to the sample signal, but has it water line shapes slightly different in shape and positions. Therefore, a direct subtraction, or a ratio comparison using the reference data without correction may have water vapor artifacts. The amount of the water in the reference signal can be measured as accurately as in the sample signal so that real time corrections are possible using stored data and several different mathematical models to correct the line shapes and offset.

In certain embodiments, mathematical model correction strategies may be employed. One is to use the reference spectra as the background measurement after correction. This works because the reference signal has a noise level that is smaller or about the same as the sample spectra. A mathematical convolution correcting the water lines shape and position is practical because the error is unchanging with time. The fixed differences in background shape caused by each different sampling accessory do not change with time, allowing a stored difference file generated with that sampling accessory to be used to correct mathematically the overall shape of the reference detector background measurement generated at the time the sample data is collected, allowing it to be used as a real time background file. The simultaneous collection of background and sample data provides good water vapor artifact suppression.

Another water vapor artifact removal technique would be to measure and store many background spectra collected though the sample optics. Each of these stored background measurements would be collected with a different amount of water vapor in the purge gas. In certain embodiments, the water vapor is maintained at a constant level for each individual background measurement. These stored background spectra can later be used as background to ratio against a sample collected at a later time. With each of these stored background measurements, matching reference spectra is collected.

The system software would measure the real time water vapor level in the reference beam, and use that data to select the correct stored sample background measurement for the ratioing process. In order to limit number of stored spectra, a mathematical interpolating process can be used to provide a better fit to the amount of water vapor in the stored reference spectra and the real time collected spectra. In certain embodiments, the user could use such a process with about 25 sample and reference spectra with varying amounts of water vapor stored for each sampling accessory.

In certain embodiments, an FTIR instrument could be set up in a factory environment, and automatic calibration would be done there with a special water vapor controlled test fixture. If the system was later upgraded with a new sampling accessory, the stored background data could be collected and stored in a standard system that stays in the factory so that the accessory could be installed in the field and the stored spectra added to memory without the need for special calibration runs in the field.

Various other modifications and alterations in the structure and method of operation of this invention will be apparent to those skilled in the art without departing from the scope and the spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A spectroscopy system, comprising:
an interferogram source to provide an IR signal containing an interferogram;
a source path including a focal point along a path axis of a first portion of an optical path extending from said interferogram source;
a Jacquinot stop including an aperture disposed substantially at said focal point, and a reflective surface substantially non-orthogonal to said path axis and facing said interferogram source, wherein said aperture passes an inner portion of said IR signal as an incident portion of said IR signal, and said reflective surface reflects an outer portion of said IR signal as a reflected portion of said IR signal; and a reference detection device to detect said reflected portion of said IR signal.

2. The spectroscopy system of claim 1, wherein:
said aperture comprises an optical opening to pass a radially inward portion of said IR signal; and
said reflective surface reflects a radially outward portion of said IR signal.

3. The spectroscopy system of claim 1, wherein:
said reflective surface comprises a curved surface; and
said aperture is disposed near a vertex of said curved surface.

4. The spectroscopy system of claim 1, wherein said interferogram source comprises:
an infrared (IR) source to emit IR energy;
an interferometer to produce and combine fixed and variable reflections of said IR energy; and
a mirror disposed to reflect said combined fixed and variable reflections of said IR energy.

5. The spectroscopy system of claim 1, wherein said interferogram source comprises a Michelson interferometer.

6. The spectroscopy system of claim 1, wherein said reference detection device comprises an infrared detector.

7. The spectroscopy system of claim 1, wherein said reference detection device comprises:
a mirror disposed to further reflect said reflected portion of said IR signal; and
an infrared detector to receive said further reflected portion of said IR signal.

8. The spectroscopy system of claim 1, further comprising a sample detection device to detect at least a portion of said IR signal.

9. The spectroscopy system of claim 8, wherein said sample detection device comprises an infrared detector.

10. The spectroscopy system of claim 8, wherein said sample detection device comprises:
a mirror disposed to reflect said at least a portion of said IR signal; and
an infrared detector to receive said reflected at least a portion of said IR signal.

11. A spectroscopy method, comprising:
generating, with an interferogram source, an IR signal containing an interferogram;
conveying said IR signal via a light path including a focal point along a path axis of a first portion of an optical path extending from said interferogram source;
passing an inner portion of said IR signal as an incident portion of said IR signal via an aperture of a Jacquinot stop disposed substantially at said focal point and including a reflective surface substantially non-orthogonal to said path axis and facing said interferogram source;
reflecting, via said reflective surface, an outer portion of said IR signal as a reflected portion of said IR signal; and
detecting said reflected portion of said IR signal.

12. The spectroscopy method of claim 11, wherein:
said passing an inner portion of said IR signal via an aperture passing a radially inward portion of said IR signal via an optical opening; and
said reflecting, via said reflective surface, an outer portion of said IR signal comprises reflecting a radially outward portion of said IR signal.

13. The spectroscopy method of claim 12, wherein:
said reflecting a radially outward portion of said IR signal comprises reflecting said radially outward portion of said IR signal via a curved surface; and
said passing a radially inward portion of said IR signal via an optical opening comprises passing a radially inward portion of said IR signal at a vertex of said curved surface.

14. The spectroscopy method of claim 11, wherein said generating, with an interferogram source, an IR signal containing an interferogram comprises:
generating IR energy;
producing and combining fixed and variable reflections of said IR energy; and
reflecting said combined fixed and variable reflections of said IR energy.

15. The spectroscopy method of claim 11, wherein said generating, with an interferogram source, an IR signal containing an interferogram comprises generating said IR signal with a Michelson interferometer.

16. The spectroscopy method of claim 11, wherein said detecting said reflected portion of said interferogram comprises receiving said reflected portion of said interferogram with an infrared detector.

17. The spectroscopy method of claim 11, wherein said detecting said reflected portion of said IR signal comprises:
further reflecting said reflected portion of said IR signal; and
receiving said further reflected portion of said IR signal with an infrared detector.

18. The spectroscopy method of claim 11, further comprising detecting at least a portion of said IR signal.

19. The spectroscopy method of claim 18, wherein said detecting at least a portion of said IR signal comprises receiving said at least a portion of said IR signal with an infrared detector.

20. The spectroscopy method of claim 18, wherein said detecting at least a portion of said IR signal comprises:
reflecting said at least a portion of said IR signal; and
receiving said reflected at least a portion of said IR signal with an infrared detector.

* * * * *